(12) United States Patent
Gronau et al.

(10) Patent No.: US 8,915,876 B2
(45) Date of Patent: Dec. 23, 2014

(54) METHOD FOR REMOVING BLOOD FROM AN EXTRACORPOREAL BLOOD CIRCUIT AS WELL AS APPARATUSES

(75) Inventors: Soeren Gronau, Nauheim (DE);
Juergen Haecker, Neu-Anspach (DE);
Ralf Mueller, Bad Homburg (DE);
Manfred Weis, St. Wendel (DE); Stefan Kreber, Saarbruecken (DE); Martin Thys, Grettstadt (DE)

(73) Assignee: Fresenius Medical Care Deutschland GmbH, Bad Homburgh (DE)

( * ) Notice: Subject to any disclaimer, the term of this patent is extended or adjusted under 35 U.S.C. 154(b) by 168 days.

(21) Appl. No.: 13/560,100

(22) Filed: Jul. 27, 2012

(65) Prior Publication Data
US 2013/0030346 A1 Jan. 31, 2013

Related U.S. Application Data

(60) Provisional application No. 61/512,930, filed on Jul. 29, 2011.

(30) Foreign Application Priority Data

Jul. 29, 2011 (DE) .......................... 10 2011 108 777

(51) Int. Cl.
*A61M 37/00* (2006.01)
*A61M 1/36* (2006.01)
*A61M 1/34* (2006.01)

(52) U.S. Cl.
CPC ............. *A61M 1/3643* (2013.01); *A61M 1/342* (2013.01); *A61M 1/3646* (2014.02); *A61M 2205/123* (2013.01); *A61M 2205/3334* (2013.01); *A61M 2230/30* (2013.01)
USPC ........ 604/6.09; 604/6.06; 604/6.11; 604/5.04

(58) Field of Classification Search
CPC ............ A61M 1/3643; A61M 1/3646; A61M 2230/30; A61M 2205/123; A61M 2205/3334; A61M 1/342
USPC .............................. 604/6.09, 6.06, 6.11, 5.04
See application file for complete search history.

(56) References Cited

U.S. PATENT DOCUMENTS

| 4,552,721 A | 11/1985 | Fentress et al. |
|---|---|---|
| 2002/0147440 A1 | 10/2002 | Samolyk |
| 2008/0149551 A1 | 6/2008 | Brugger et al. |
| 2010/0274172 A1 | 10/2010 | Guenther et al. |

FOREIGN PATENT DOCUMENTS

| DE | 102006012087 A1 | 9/2007 |
|---|---|---|
| DE | 102009008346 A1 | 8/2010 |

(Continued)

*Primary Examiner* — Tatyana Zalukaeva
*Assistant Examiner* — Andrew J Mensh
(74) *Attorney, Agent, or Firm* — Kenyon & Kenyon LLP

(57) ABSTRACT

The present invention relates to a method for removing blood from an extracorporeal blood circuit and/or a functional device, each connectable or connected with a blood treatment apparatus for the purpose of blood treatment of a patient. The blood treatment apparatus of the method comprises or is connected with at least one extracorporeal blood circuit with a line having interior portions, the extracorporeal blood circuit comprising at least one arterial line section and at least one venous line section, wherein a first section of the arterial line section is configured to be connected with a second section of the venous line section, and further comprises at least one blood pump for conveying blood within the line interior portions. The method includes the step of operating the blood pump in a second conveying direction which is opposite to a first customary conveying direction. It further relates to corresponding apparatuses.

17 Claims, 1 Drawing Sheet

(56) References Cited

FOREIGN PATENT DOCUMENTS

| | | |
|---|---|---|
| DE | 102009018664 A1 | 10/2010 |
| DE | 102009024468 A1 | 12/2010 |
| DE | 102009024606 A1 * | 12/2010 |
| EP | 0578175 A1 | 1/1994 |

* cited by examiner

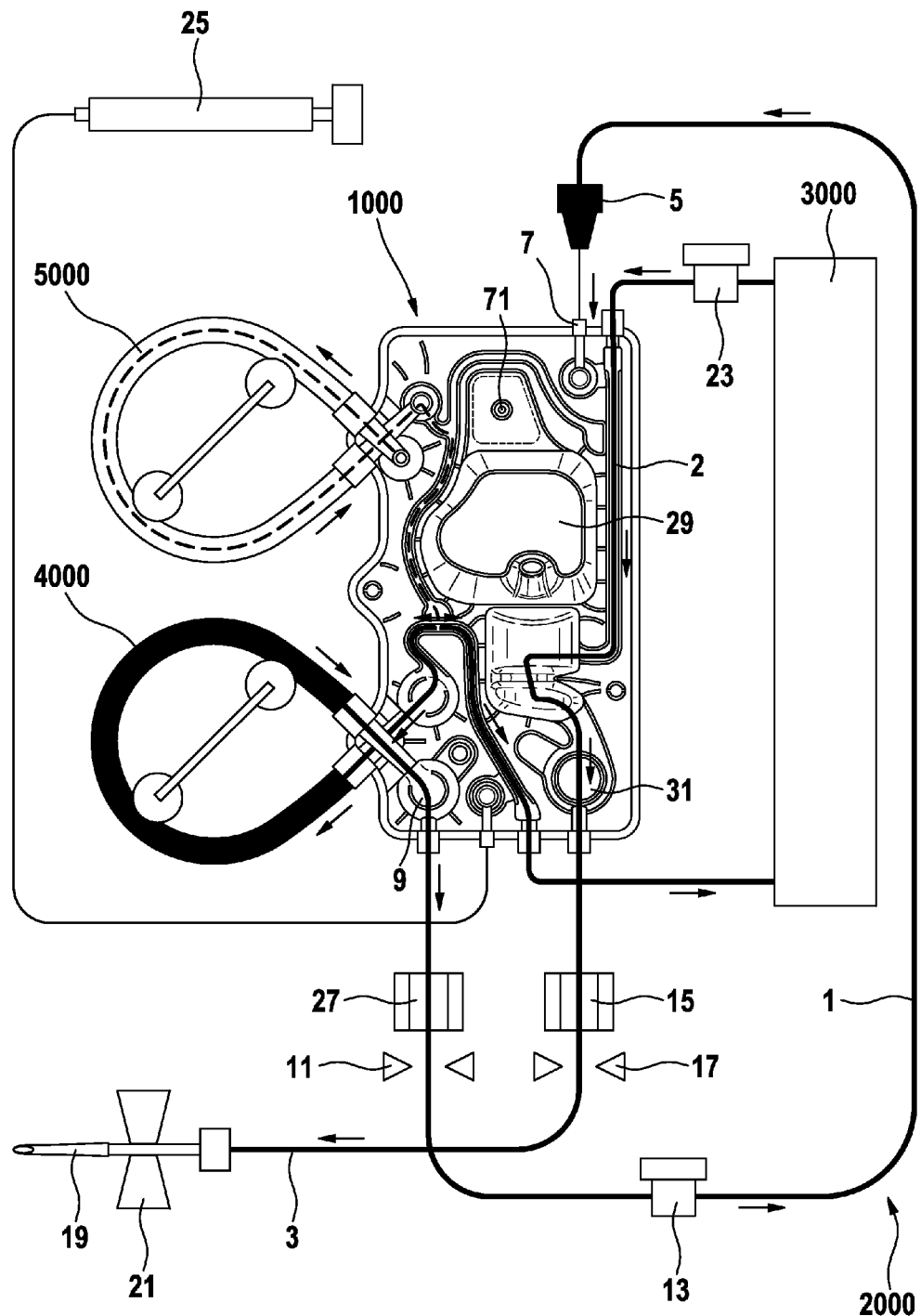

METHOD FOR REMOVING BLOOD FROM AN EXTRACORPOREAL BLOOD CIRCUIT AS WELL AS APPARATUSES

CROSS REFERENCE TO RELATED APPLICATIONS

This application claims the benefit of U.S. Provisional Patent Application No. 61/512,930 filed on Jul. 29, 2011 and German Patent Application No. 10 2011 108 777.3, filed Jul. 29, 2011, both of which are herein incorporated by reference in their entireties.

FIELD OF INVENTION

The present invention relates to a method for removing blood from an extracorporeal blood circuit and/or from a functional device, each of which is connectable or connected with a blood treatment apparatus for the purpose of a blood treatment of a patient. In addition, it relates to systems and computer media for performing methods in accordance with the present invention.

BACKGROUND OF INVENTION

Not least for hygienic reasons, blood remaining in the blood circuit after use of extracorporeal blood circuits is regularly removed therefrom.

One object of the present invention is to specify a further method for removing blood from an extracorporeal blood circuit or from a functional device at the end of a blood treatment session.

Further, a blood treatment apparatus by means of which the method according to the invention is feasible as well as control device provided for executing the method according to the invention, a suitable digital storage medium, a suitable computer program product and a suitable computer program are to be specified.

All advantages that are achievable by means of the method according to the invention may in certain embodiments according to the invention undiminishedly also be achieved by means of the apparatuses according to the invention.

The method according to the invention is suitable and intended for removing blood from an extracorporeal blood circuit which comprises at least one arterial line section and at least one venous line section, and/or for removing blood from a functional device which is or are connectable or connected with a blood treatment apparatus for the purpose of a blood treatment of a patient, or each from sections thereof.

The method according to the invention encompasses conveying the fluid present in the extracorporeal blood circuit after the end of the treatment by means of a blood pump which was already used for the blood treatment. While the blood pump conveyed fluid in a first conveying direction during the blood treatment, conveying in the method according to the invention takes place by means of the blood pump in a second conveying direction which is opposite to the first conveying direction. For executing the method according to the invention, a first section of the arterial line section is or will be connected with a second section of the venous line section of the extracorporeal blood circuit.

The functional device according to the invention, which in particular is embodied as a blood cassette, comprises a venous line section and a venous addition point communicating herewith. The venous addition point is prepared and/or provided to be connected with an arterial needle connection of the arterial line section of an extracorporeal blood circuit.

The set according to the invention comprises at least one functional device according to the invention and at least one extracorporeal blood circuit. The arterial needle connection or a different section of the arterial line section of the extracorporeal blood circuit is prepared to be connected with the venous addition point of the functional device.

The blood treatment apparatus according to the invention is provided and embodied and/or equipped for executing the method according to the invention.

The control device according to the invention is suitable and provided and/or arranged and/or configured for executing the method according to the invention.

A digital, particularly a non-volatile storage medium according to the invention, particularly in the form of a machine-readable data storage device, particularly in the form of a disk, CD, EPROM or DVD, with electrically readable control signals may interact with a programmable computer system such that the mechanical steps of a method according to the invention are prompted. According to the invention a computer program product can be understood as, for example, a computer program which is stored on a storage device, an embedded system as a comprehensive system with a computer program (e.g. an electronic device with a computer program), a network of computer-implemented computer programs (e.g. a client-server system, a cloud computing system, etc.), or a computer on which a computer product is loaded, executed, saved or developed. In doing so, all or some of the mechanically executed steps of the method according to the invention may be prompted.

A computer program product according to the invention comprises a program code—e.g., volatile, transitory or non-transitory and saved on a machine-readable medium—for prompting the mechanical steps of the method according to the invention when the computer program product runs on a computer.

The term "machine-readable medium" as used herein denotes in certain embodiments of the present invention a medium containing data or information which is interpretable by software and/or hardware. The medium may be a data medium, like a disk, a CD, DVD, a USB stick, a flashcard, an SD card or the like.

A computer program according to the invention comprises a program code for prompting the mechanical steps of a method according to the invention when the computer program runs on a computer. A computer program according to the present invention can be understood as, for example, a physical software product, which is ready for distribution and contains a computer program.

It also applies for the computer program product according to the invention and the computer program according to the invention that all or some of the mechanically executed steps of the method according to the invention are prompted.

Embodiments according to the invention may comprise some or all of the following features in arbitrary combination. Advantageous developments of the present invention are each also subject of the dependent claims.

In all of the following embodiments, the use of the expression "may be" or "may have" and so on, is to be understood synonymously with "preferably is" or "preferably has," respectively, and so on, and is intended to illustrate exemplary embodiments according to the invention.

The extracorporeal blood circuit is in certain embodiments of the present invention a tube set. In any case, the extracorporeal blood circuit is provided for extracorporeally conducting blood of a patient, e.g., during hemodialysis, hemofiltration, hemodiafiltration or the like.

In some embodiments according to the invention, the extracorporeal blood circuit is at least in sections embodied as an integral and, where appropriate, permanent part of the functional device, in others it is not. A freely movable tube section of the extracorporeal blood circuit may therefore continue in one piece or integrally on or in the functional device, e.g., a blood cassette, and vice versa.

A functional device is in certain embodiments of the present invention a device which is used in a blood treatment. Examples of functional devices include internal and external functional devices, medical disposables, in particular blood cassettes such as a disposable blood cassette, or other blood-conducting devices.

Exemplary embodiments of a blood cassette are in particular disclosed in the application of the Applicant with the publication number DE 10 2009 018 664 A1 having the title *Externe Funktionseinrichtung, Blutbehandlungsvorrichtung zum Aufnehmen einer erfindungsgemäßen externen Funktionseinrichtung, sowie Verfahren*, which was submitted to the German Patent and Trademark Office on Apr. 23, 2009, and in the application of the Applicant with the publication number DE 10 2009 024 468 A1 of the same title, which was submitted to the German Patent and Trademark Office on Jun. 10, 2009. The respective disclosures are herewith fully incorporated by way of reference.

In certain embodiments according to the invention, the functional device as external functional device is not a part of the blood treatment apparatus, i.e., no integral element of it. In other embodiments, the functional device may be a part of the blood treatment apparatus.

A blood treatment apparatus is provided and/or embodied for performing or prompting a medical treatment, in particular a blood treatment of the patient, e.g., a dialysis. For this purpose, the blood treatment apparatus is connected with or comprises at least one extracorporeal blood circuit which comprises a line having interior portions.

The arterial line section of the extracorporeal blood circuit is in certain embodiments of the present invention the line section in which the patient blood that leaves the body of the patient for the purpose of the extracorporeal blood treatment flows and in which it is present before it enters the blood treatment device, e.g., a dialyzer.

In certain embodiments of the present invention, the first section of the arterial line section is or comprises the arterial needle connection to the patient, e.g., the arterial needle connection in a double-needle dialysis treatment.

The venous line section of the extracorporeal blood circuit is in some embodiments of the present invention the line section from which the extracorporeally treated patient blood flows towards or back into the body of the patient after its treatment in a blood treatment device, e.g., a dialyzer.

In certain embodiments of the present invention, the second section of the venous line section is or encompasses a venous port, for example a venous addition port or a venous addition point. It may, where appropriate, be used or provided for the addition of substitute liquid, calcium citrate, heparin or the like to the patient blood flowing in the venous line section of the extracorporeal blood circuit.

In certain embodiments of the present invention, the venous addition point of the venous line section of the extracorporeal blood circuit leads, optionally directly or indirectly, into the venous line section upstream from a blood chamber and upstream from a clot catcher.

In some embodiments according to the invention, the venous addition point is an integral part of a blood cassette.

The blood treatment apparatus comprises a blood pump for conveying blood within the line interior of the extracorporeal blood circuit.

In certain embodiments of the present invention, the first conveying direction, as is customary during blood treatment, corresponds to a conveying direction from the arterial access (blood withdrawal point) of the patient to a blood treatment device, for example a blood filter or a dialyzer, and subsequently through the venous line section of the extracorporeal blood circuit to the venous access (blood return point).

The second conveying direction which is opposite the first conveying direction therefore proceeds in such embodiments from venous to arterial.

"Removing blood" denotes in certain embodiments of the present invention completely—or basically or nearly completely—or partially removing blood from the extracorporeal blood circuit at the end of a blood treatment session.

Reinfusing the blood removed from the extracorporeal blood circuit into the vascular system of the patient itself is in some embodiments of the present invention not a part of the method according to the invention, in others, however, it is.

In certain embodiments of the present invention, the blood treatment apparatus comprises at least one second conveying device. The second conveying device serves to introduce at least a second fluid which is different from the blood, for example a substitute liquid, into the line interior portions of the extracorporeal blood circuit and/or to convey the fluid herein.

Introducing the second fluid, hereafter simplifyingly—but not restrictively—denoted as substitute liquid, into the line interior of the extracorporeal blood circuit by operating the second conveying device, hereafter simplifyingly—but not restrictively—denoted as substitute pump, in certain embodiments of the present invention takes place after connecting the first section of the arterial line sections with the second section of the venous line section.

In some embodiments according to the invention, the blood pump is operated in the second conveying direction such that the flow of the substitute liquid which is or was introduced into the line interior of the extracorporeal blood circuit is separated into at least a first and a second partial flow. The first partial flow of the substitute liquid moves towards a blood treatment device, the second partial flow of the substitute liquid moves in the second conveying direction.

In certain embodiments of the present invention, the method according to the invention encompasses disconnecting the first section.

In some embodiments of the present invention, the method according to the invention encompasses connecting the first section with a venous addition point of the venous line section of the extracorporeal blood circuit or with a venous addition point of the functional device (for example the blood cassette).

In certain embodiments of the present invention, the second conveying device and the blood pump are started, in particular basically or nearly or completely, at the same time.

The feed rates of the second conveying device and the blood pump in some embodiments of the present invention are or will be set such that a section of the venous line section, e.g., from a predilution point or from a predilution valve to the venous addition point or to a point at which fluid from the venous line section and fluid from the arterial line section are joined or meet, are not emptied of blood before a section of the arterial line section, e.g., until its connection with the venous addition point or up to the point at which fluid from the venous line section is joined with fluid from the arterial line section or both fluids meet.

In certain embodiments of the present invention, the feed rate of the blood pump is (initially, always, or on average) lower than the feed rate of the second conveying device or is adjusted accordingly.

In some embodiments of the present invention, the feed rates of the blood pump and/or of the second conveying device are monitored and/or regulated by means of pressure monitoring and/or pressure measurement and/or pressure limitation during the removal of the blood.

In doing so, in certain embodiments of the present invention, the feed rate q_V_Sub of the second conveying device is set according to the formula $$q\_V\_Sub = q\_V\_BP\left(1 + \frac{V\_ven\_min}{V\_art}\right) \quad (I)$$

In formula (I), V_ven_min denotes in certain embodiments of the present invention the volume of the venous line section including the intake volume of a smallest blood treatment device (for example, with reference to various blood treatment devices to be used at a blood treatment apparatus, see below); q_V_BP denotes the feed rate of the blood pump, V_art the volume the arterial line section or section may take in.

The "smallest blood treatment device" is in certain embodiments of the present invention the blood treatment device among a multitude of blood treatment devices, e.g., blood filters or dialyzers, which are prepared for use with the considered blood treatment apparatus (e.g., concerning the present connections, admissions or addition points and so on), which may take in the least volume or the least fluid.

A typical value for q_V_Sub may result in:

$q\_V\_Sub = 50$ ml/min$(1+(60$ ml$/60$ ml$))=100$ ml.

In certain embodiments of the present invention, the feed rate of the second conveying device is set such that at the venous addition point—or at a point at which fluid from the venous line section is joined with or meets fluid from the arterial line section—blood (from a line) and substitute liquid (from a different line) of the same degree of dilution meet.

In certain embodiments of the present invention, the method according to the invention encompasses setting the feed rate q_V_Sub of the second conveying device and the feed rate q_V_BP of the blood pump towards each other—individually for each used blood treatment device—according to the formula $$\frac{q\_V\_BP}{q\_V\_Sub} = \frac{V\_art\_S\_h}{V\_Dial \cdot F + V\_art\_S\_h} \quad (II)$$

In formula (II), V_art_S_h indicates the substitute volume which has to be conveyed into the arterial line section so that at the end of the arterial line section a hematocrite (HKT) value of ~0.02 occurs; V_Dial indicates the volume of the blood treatment device, and F indicates a dimensionless correction factor which indicates the ratio of the actual amount of liquid required for rinsing the blood treatment device (until a hematocrite HKT of about 0.02 is reached) to its nominal filling volume on the patient side.

V_art_S_h may have been or may be experimentally determined once for an averaged patient hematocrite. The same applies for the dimensionless factor F.

A typical value for q_V_BP/q_V_Sub may result in:

$q\_V\_BP/q\_V\_Sub=60$ ml$/(80$ ml$*1.5+60$ ml$)=\frac{1}{3}$.

In certain embodiments of the method according to the invention, the intention is to stop the blood pump or reduce its feed speed or feed rate, before substitute liquid downstream (with regard to the second conveying direction or to the method according to the invention) from the venous addition point or the point at which fluid from the venous line section and fluid from the arterial line section are joined or meet.

This may in certain embodiments of the present invention advantageously contribute to a stronger and/or improved flushing of the blood treatment device.

The time for stopping the blood pump or for reducing its feed rate is in certain embodiments of the present invention determined with the aid of the arterial air bubble detector/optical detector (also known as ABD/OD) which is integrated in the extracorporeal blood circuit. This may advantageously increase the accuracy of determination of the time for stopping.

In other embodiments of the present invention, the method according to the invention encompasses stopping the second conveying device or reducing the speed or the feed rate of the second conveying device before substitute liquid gets downstream (with regard to the second conveying direction or to the method according to the invention) from the venous addition point or the point at which fluid from the venous line section and fluid from the arterial line section are joined or meet. This may advantageously contribute to a stronger and/or improved flushing of the arterial line section of the extracorporeal blood circuit. The blood pump is further operated in such embodiments, or it is not further operated.

In certain embodiments of the present invention, the method according to the invention encompasses checking the connection of the first section, e.g., of the arterial needle connection, of the extracorporeal blood circuit at the venous addition point of the venous line section of the extracorporeal blood circuit (connection test).

In certain embodiments of the present invention, checking encompasses creating a pressure balance.

In such embodiments the intention may be to stop the blood pump and/or the second conveying device. Further, the intention may be to open or keep the arterial clamp open.

In certain further embodiments of the present invention, checking encompasses determining a diastolic patient pressure. A minimum value of the diastolic patient pressure may be saved over a time period of, e.g., 2.5 s. Subsequently, a negative pressure is created by means of the blood pump which conveys in the first conveying direction, i.e. forwards, wherein the venous clamp is opened or is already open. In certain embodiments of the present invention, it is defined that the vascular pressure of the patient has to drop by 50 mmHg within a time period of 2.1 s in order for the connection test to be considered to be passed. Alternatively, other values for pressure drop and/or times than the ones named here may be considered. If the desired and/or required pressure reduction has taken place not at all or not within the predetermined time, the connection test may be considered to be failed.

The functional device according to the invention is in some embodiments according to the invention embodied as disposable.

In certain embodiments according to the invention, the venous addition point of the functional device is embodied to create a fluid connection by simply clamping, attaching or screwing together an arterial needle connection or another section of the arterial line section of the extracorporeal blood circuit.

In some embodiments according to the invention, the venous addition point of the functional device and the arterial needle connection or another section of the arterial line section of the extracorporeal blood circuit are from the same connector system, e.g., Luer connectors, or female and male connector.

In certain embodiments according to the invention, the connection geometry of the venous addition point is embodied the same as or corresponds to the connection geometry of an arterial needle by means of which the extracorporeal blood circuit is connected for its use.

The control device according to the invention is in some embodiments according to the invention embodied as a regulating device.

The blood treatment device according to the invention is in some embodiments according to the invention embodied as a hemodialysis apparatus or hemofiltration apparatus or hemodiafiltration apparatus.

The blood treatment device according to the invention comprises in certain embodiments according to the invention at least one control device according to the invention.

Some or all embodiments according to the invention may comprise one, more or all of the advantages named above and/or hereafter.

The present invention provides a simple and not very elaborate method for removing blood from an extracorporeal blood circuit after a blood treatment session as well as corresponding apparatuses. By removing blood at the end of the treatment, the risk of contamination may advantageously be reduced during further use or disposing of the blood circuit.

In certain embodiments according to the invention, the method allows for completely returning blood present in the extracorporeal blood circuit at the end of the blood treatment session to the vascular system of the patient via a venous connection with the vascular system of the patient. Infusing substitute liquid or another fluid to the patient at the same time is hereby preventable.

The method according to the invention may advantageously be implemented in treatment apparatuses already known from practice just by means of a simple to perform software update. The blood treatment apparatuses known from practice often already comprise the required machine elements.

BRIEF DESCRIPTION OF THE FIGURE

Hereafter, the present invention is exemplarily described with reference to the appended figure. It applies that:

FIG. 1 shows in simplified illustration a medical functional device with an extracorporeal blood circuit, which may be cleared of blood by means of the method according to the invention.

DETAILED DESCRIPTION

FIG. 1 shows a schematically simplified functional device 1000 with an extracorporeal blood circuit 2000 connected herewith.

The extracorporeal blood circuit 2000 comprises or is connected with a blood treatment device 3000, e.g., a blood filter or dialyzer.

A blood treatment apparatus represented in FIG. 1 only by means of some of its devices, by means of which the method described here is automatically completely or mostly executed by means of reinfusing blood contained in the extracorporeal blood circuit 2000, comprises a blood pump 4000 and a second conveying device 5000. Both the blood pump 2000 and the second conveying device 5000 convey fluid through sections of the functional device 1000 and of the extracorporeal blood circuit 2000. The functional device 1000 is exemplarily a blood cassette.

Indicated is a connection diagram as well as flow directions, specified by arrows, of blood and substituate (as an example for a second fluid) during removal of the blood with a simultaneous reinfusion of the blood. The only double arrow describes a split of the substituate flow into two partial flows.

The extracorporeal blood circuit 2000 comprises an arterial line section 1 as well as a venous line section 3.

The arterial line section 1 comprises a first section. The first section is in the example of FIG. 1 exemplarily embodied as an arterial needle connection 5.

The venous line section 3 comprises a second section. The second section 3 is in FIG. 1 exemplarily embodied as venous addition point 7 of the functional device 1000.

The arterial line section 1 comprises an arterial pressure sensor which is coupled to the functional device 1000 at the location denoted with the reference numeral 9 without itself being a part of the functional device 1000. This pressure sensor serves to measure the pressure or to determine the pressure drop during a connection test. It is arranged in the arterial line section 1 of the extracorporeal blood circuit 2000.

The arterial line section 1 comprises an arterial clamp 11.

The arterial line section 1 comprises an arterial septum 13.

The venous line section 3 comprises a venous air bubble detector/optical sensor 15.

The venous line section 3 comprises a venous clamp 17.

The venous line section 3 comprises a venous needle 19 on a venous patient connector 21.

A venous septum 23 is arranged between the blood treatment device 3000 and the location of its connection with the section of the extracorporeal blood circuit 2000 present on the functional device 1000.

For adding heparin into the line interior of the extracorporeal blood circuit 2000 during an extracorporeal blood treatment, the extracorporeal blood circuit 2000 is connected with a heparin syringe 25 via a corresponding port of the functional device 1000.

The arterial line section 1 comprises an arterial air bubble detector optical sensor 27.

During the blood treatment, the extracorporeal blood circuit 2000 is, e.g., as is shown in FIG. 1 in the form of a tube system, connected with the vascular system of the patient via two needles (in the case of a double-needle dialysis). For performing the blood treatment, the extracorporeal blood circuit 2000 is filled with blood of the patient and this blood flows through the extracorporeal blood circuit 2000 during the treatment.

Hereafter, removal according to the invention of blood from the extracorporeal blood circuit by using the venous addition point 7 of the functional device 1000 is described. In the example of a mechanically executed embodiment of the method as described here, reinfusion of the blood takes place simultaneously with the removal of this blood.

The method according to the invention may be started automatically or manually by the doctor.

For this purpose, in certain embodiments of the invention, the arterial patient connector is disconnected from the arterial needle connection 5 at the end of the blood treatment and connected in fluid connection with a port of the blood cassette, here the venous addition point 7. As may be taken from the blood cassette shown in FIG. 1, the venous addition point 7 may lead directly (in other embodiments also indirectly, however) into the venous line section 3 of the extracorporeal blood circuit 2000 upstream from a blood chamber 29 and from a clot catcher 31.

The venous addition point 7 is in the above-named applications of the Applicant with the publication numbers DE 10 2009 018 664 A1 and DE 10 2009 024 468 A2 each in FIGS. 1 and 2 marked with the reference numeral 37. The venous addition point 7 is in connection with the venous filter line via a non-return valve.

The user may be prompted towards the end of the blood treatment to disconnect the arterial needle connection 5 from the arterial patient connector (not shown in FIG. 1) and screw the arterial needle connection 5 onto the Luer connector of the venous addition point 7 of the functional device 1000. In order to check whether the connection is made correctly, a connection test may be performed by the blood treatment apparatus automatically or upon request. In doing so, the correct connection of the arterial line section 1 with the venous line section 3 is checked. Directly conveying the blood via the arterial line section 1 into the vascular system of the patient may therefore advantageously be prevented.

The venous line section 3 is in certain embodiments provided with a non-return valve, which is why the blood pump 4000 cannot draw in liquid from the venous line section 3 in the first conveying direction. It may therefore be expected that during performance of the connection test the pressure in the arterial line section 1 decreases. If the arterial pressure decreases as expected, it can be assumed that the patient is no longer arterially connected, at least that the (manual) arterial (tube) clamp 11 is closed.

If, as is the case in certain embodiments of the present invention, an arterial pressure alarm during conveying is provided in this stage of the method, an error would advantageously be detected also early on, even without a connection test. Thus, it may advantageously be possible to forego explicitly testing the connection state.

The connection test for detecting whether the arterial line section 1, e.g., by means of the arterial needle connection 5, is connected with the venous line section 3, e.g., the venous addition point 7, may hereby take place in detail as described hereafter: At first, a pressure balance is created, wherein the blood pump 4000 and the second conveying device 5000 are stopped. The arterial clamp 11 is open.

By means of a pressure sensor, the diastolic patient pressure is detected. Hereby, a minimum value is saved over 2.5 s. Subsequently, a negative pressure is built up, whereby the venous clamp 17 is opened and whereby the blood pump 4000 operates The pressure has to drop below the diastolic patient pressure as detected before, e.g., by 50 mmHg within 2.1 s, otherwise the connection test is considered to be failed.

A predilution valve or predilution connection, provided for introducing substitute liquid into the blood line between the blood treatment device 3000 and the blood pump 4000 is opened for removing blood according to the invention. The substitute line is connected with the predilution connection, so that the second conveying device 5000 can introduce substituate solution into a section of the extracorporeal blood circuit 2000 which is located between the blood pump 4000 and the blood treatment device 3000.

In the embodiment illustrated here, the blood pump 4000 starts at the same time (simultaneously) the second conveying device 5000 starts conveying backwards, i.e. in the second conveying direction at a lower feed rate. In doing so, the substituate flow is split due to the different feed speeds of the two pumps—one partial flow of the substituate solution moves towards the blood pump 4000, another partial flow of the substituate solution moves in the direction towards the blood treatment device 3000.

The occurring venous and/or arterial pressures are monitored during this process. The set pump rates or feed rates of the conveying devices (blood pump 4000 and second conveying device 5000) may have a considerable effect on the removal of the blood.

In certain embodiments of the present invention, it is ensured that the feed rate of the blood pump 4000 is not selected to be too high. Thus, it may advantageously be ensured that the blood is not damaged when it flows through the point of introduction—e.g., provided with a thinner tube and a non-return valve. For this, a limitation of the maximum feed rate, for example based on experience from in vitro tests, is possible or provided.

In some embodiments of the present invention, a limitation and/or monitoring the pressure drop across the addition point and/or the addition line and the non-return valve is possible with the aid of the arterial pressure sensor 9 during reinfusion.

When setting the "venous" reinfusion rate, i.e. the speed by means of which the blood which is present extracorporeally is conveyed towards the patient via the venous line section 3 of the extracorporeal blood circuit 2000, it is in some embodiments according to the invention ensured that the part of the extracorporeal blood circuit 2000 which extends from the predilution point or the predilution valve to the venous addition point is not emptied earlier than or before the arterial line section 1 of the extracorporeal blood circuit 2000 is also emptied.

Hereby, in certain embodiments of the present invention, a further commingling of blood (arterial) and substituate liquid (venous) and, along with this, an unnecessary increase of the reinfusion volume with the known unpleasant consequences for the patient may advantageously be prevented.

As the volumes of the individual line sections of an extracorporeal blood circuit (also denoted as tube set) are known, it is in certain embodiments of the present invention provided to calculate the maximum possible or permissible venous feed rate as the feed rate in the venous line section of the extracorporeal blood circuit 2000. The calculation may be carried out as described above.

The venous feed rate is in some embodiments of the present invention set by means of the feed rate $q\_V\_Sub$ of the second conveying device 5000 (substituate pump) deducting the feed rate $q\_V\_BP$ of the blood pump 4000. For this purpose, reference is made to the formulas above.

As with such a fixed specification of the volume of the blood treatment device 3000 the arterial line section 1 of the extracorporeal blood circuit 2000 may be emptied earlier or faster than the venous line section 3, it is in certain embodiments of the present invention suggested to stop the blood pump 4000 before substituate liquid is conveyed across the venous addition point 7.

Such stopping of the conveying by means of the blood pump 4000 is in certain embodiments possible by means of the corresponding adjustment of the feed rate of the blood pump 4000, if the above-mentioned volume is known. Waiting for the moment in which the blood pump 4000 may be stopped—where applicable advantageously more precise—is also possible considering the signals of the arterial air bubble detector or optical sensor 11—if existent.

In some embodiments according to the invention, the feed rate of the second conveying device 5000 is increased from the time of stopping the blood pump 4000 with the advantage of saving time.

If the volume of the utilized blood treatment device 3000 is known, the feed rate is advantageously set individually to the maximum possible feed rate with each reinfusion. This shortens the period of time the patient and the operating personnel have to spend at the blood treatment apparatus until the completion of this measure, due to the faster removal of blood from the extracorporeal blood circuit 2000.

The type of the utilized blood treatment device 3000 may be set by the operating personnel. Alternatively, the utilized type may be automatically determined by means of certain parameters which can be observed when filling the blood treatment device 3000.

If the volume of the blood treatment device 3000 is known, in some embodiments according to the invention, the feed rate of the second conveying device 5000 is set such that at the point of introduction of the venous addition point 7 (or at a comparable point in the blood circuit) substituate and blood of the same dilution degree from both line sections 1, 3 meet at the same time. The blood pump 4000 may subsequently either be stopped; alternatively, it continues to run.

In embodiments in which the blood pump 4000 continues to run, the arterial line section 1 of the extracorporeal blood circuit 2000 is advantageously comparatively flushed better; in embodiments in which the blood pump 4000 is stopped, the blood treatment device 3000 is advantageously comparatively flushed better.

In certain embodiments, the individual setting of the feed rates takes place according to the above-named formula (II).

What is claimed is:

1. A method for removing blood from an extracorporeal blood circuit and/or a functional device at the end of a blood treatment session, each of said extracorporeal blood circuit and/or functional device being connectable or connected with a blood treatment apparatus for the purpose of blood treatment of a patient, wherein the blood treatment apparatus comprises or is connected with: at least one extracorporeal blood circuit with a line having interior portions, wherein the extracorporeal blood circuit comprises at least one arterial line section and at least one venous line section, a first section of the arterial line section and a second section of the venous line section being connected or configured to be connected; and, at least one blood pump for conveying blood within the line interior portions of the extracorporeal blood circuit; wherein the method comprises the steps of: operating the blood pump in a second conveying direction which is opposite to a first conveying direction of the blood pump which is customary during the blood treatment; disconnecting an arterial needle connection of the arterial line section of the extracorporeal blood circuit from the patient; and connecting the arterial needle connection of the extracorporeal blood circuit with a venous addition point of the venous line section of the extracorporeal blood circuit.

2. The method according to claim 1, wherein the blood treatment apparatus comprises at least one second conveying device for introducing a second fluid into line interior portions of the extracorporeal blood circuit and/or for conveying a line content within line interior portions of the extracorporeal blood circuit, the method further comprising the step of:
   introducing the second fluid into line interior portions of the extracorporeal blood circuit by operating the second conveying device after the first section of the arterial line section was connected with a second section of the venous line section.

3. The method according to claim 2, wherein the second conveying device and the blood pump are started at the same time.

4. The method according claim 2, wherein a feed rate of the blood pump and a feed rate of the second conveying device are set such that the venous line section is not emptied before the arterial line section.

5. The method according to claim 2, wherein a feed rate of the blood pump is smaller than a feed rate of the second conveying device.

6. The method according to claim 2, wherein a feed rate of the blood pump and a feed rate of the second conveying device are monitored and/or regulated by means of pressure monitoring and/or pressure measurement and/or pressure limitation during removal of the blood.

7. The method according to claim 2, wherein a feed rate of the second conveying device is set according to the formula $$q\_V\_Sub = q\_V\_BP\left(1 + \frac{V\_ven\_min}{V\_art}\right)$$

wherein
   q_V_Sub is the feed rate of the second conveying device;
   q_V_BP is the feed rate of the blood pump;
   V_ven_min indicates the volume of the venous line section with a minimum or smallest blood treatment device; and
   wherein
   V_art indicates the volume the arterial line section or section may take in.

8. The method according to claim 2, further comprising the step of:
   setting a feed rate of the second conveying device such that at the venous addition point or at a point at which fluid from the venous line section and fluid from the arterial line section are joined or meet, blood and second fluid of the same dilution degree meet.

9. The method according to claim 2, further comprising the step of:
   setting a feed rate of the blood pump and a feed rate of the conveying device individually for the utilized blood treatment device according to the formula $$\frac{q\_V\_BP}{q\_V\_Sub} = \frac{V\_art\_S\_h}{V\_Dial \cdot F + V\_art\_S\_h}$$

wherein
   q_V_Sub is the feed rate of the second conveying device;
   q_V_BP is the feed rate of the blood pump;
   V_art_S_h indicates the substituate volume which has to be conveyed into the arterial line section so that at the end of the arterial line section, a hematocrit value of ~0.02 occurs;
   V_Dial indicates the volume of the blood treatment device; and
   F indicates a dimensionless correction factor which indicates the relation of the actually required amount of liquid for rinsing the blood treatment device up to hematocrit value of ~0.02 to its nominal filling volume on the patient side.

10. The method according to claim 9, wherein V_art_S_h and/or the factor F are or were determined experimentally once for an average patient hematocrit.

11. The method according to claim 2, further comprising the step of:
   stopping the blood pump before second fluid is introduced into the venous line section of the extracorporeal blood circuit at the venous addition point, or before the second fluid reaches a point at which fluid from the venous line section and fluid from the arterial line section are joined or meet;

or stopping the second conveying device before the second fluid is introduced into the venous line section of the extracorporeal blood circuit at the venous addition point, or before the second fluid reaches a point at which fluid from the venous line section and fluid from the arterial line section are joined or meet.

12. The method according to claim 1, further comprising the step of:

checking the connection of the arterial needle connection of the extracorporeal blood circuit with the venous addition point of the extracorporeal blood circuit.

13. The method according to claim 12, wherein checking comprises the steps of:

creating a pressure balance;

detecting a diastolic patient pressure; and building up a negative pressure by means of the blood pump which is conveying in a first conveying direction or forward.

14. The method according to claim 1, wherein the venous addition point of the venous line section of the extracorporeal blood circuit leads into the venous line section upstream from a blood chamber and upstream from a clot catcher.

15. A blood-handling system, said blood-handling system comprising a control device or regulating device, suitable and provided and/or arranged and/or configured for executing a method according to claim 1.

16. The blood-handling system of claim 15, wherein the blood-handling system is configured as a hemodialysis apparatus, hemofiltration apparatus or hemodiafiltration apparatus.

17. A non-transitory computer-readable medium with an executable program stored thereon, wherein the program is configured to instruct a programmable computer system to execute the method according to claim 1.

* * * * *